(12) United States Patent
Schaefer et al.

(10) Patent No.: US 11,542,356 B2
(45) Date of Patent: Jan. 3, 2023

(54) METHOD FOR PRODUCING POLYISOCYANATES OF (CYCLO)ALIPHATIC DIISOCYANATES WHICH ARE FLOCCULATION-STABLE IN SOLVENTS

(71) Applicant: BASF SE, Ludwigshafen am Rhein (DE)

(72) Inventors: Harald Schaefer, Ludwigshafen (DE); Thomas Genger, Ludwigshafen (DE); Sebastian Emmerling, Ludwigshafen (DE)

(73) Assignee: BASF SE

( * ) Notice: Subject to any disclaimer, the term of this patent is extended or adjusted under 35 U.S.C. 154(b) by 0 days.

(21) Appl. No.: 16/648,451

(22) PCT Filed: Sep. 11, 2018

(86) PCT No.: PCT/EP2018/074385
§ 371 (c)(1),
(2) Date: Mar. 18, 2020

(87) PCT Pub. No.: WO2019/057540
PCT Pub. Date: Mar. 28, 2019

(65) Prior Publication Data
US 2020/0223971 A1  Jul. 16, 2020

(30) Foreign Application Priority Data
Sep. 20, 2017 (EP) .................... 17192030

(51) Int. Cl.
| | | |
|---|---|---|
| *C08G 18/02* | (2006.01) | |
| *C08G 18/08* | (2006.01) | |
| *C08G 18/73* | (2006.01) | |
| *C08G 18/78* | (2006.01) | |
| *C08G 18/79* | (2006.01) | |
| *C08K 5/5415* | (2006.01) | |
| *C09D 175/04* | (2006.01) | |
| *C07C 265/04* | (2006.01) | |
| *C07C 269/08* | (2006.01) | |
| *C08K 5/521* | (2006.01) | |

(52) U.S. Cl.
CPC .......... *C08G 18/022* (2013.01); *C07C 265/04* (2013.01); *C07C 269/08* (2013.01); *C08G 18/0847* (2013.01); *C08G 18/0885* (2013.01); *C08G 18/73* (2013.01); *C08G 18/7831* (2013.01); *C08G 18/7837* (2013.01); *C08G 18/7887* (2013.01); *C08G 18/791* (2013.01); *C08G 18/792* (2013.01); *C08K 5/5415* (2013.01); *C09D 175/04* (2013.01); *C08K 5/521* (2013.01)

(58) Field of Classification Search
CPC .............. C08G 18/022; C08G 18/0847; C08G 18/0885; C08G 18/73; C08G 18/7831; C08G 18/7837; C08G 18/7887; C08G 18/791; C08G 18/792; C08K 5/5415; C08K 5/521; C09D 175/04; C07C 265/04; C07C 269/08
See application file for complete search history.

(56) References Cited

U.S. PATENT DOCUMENTS

| | | |
|---|---|---|
| 4,596,678 A | 6/1986 | Merger et al. |
| 5,087,739 A | 2/1992 | Bohmholdt et al. |
| 5,202,358 A | 4/1993 | Scholl et al. |
| 5,260,481 A | 11/1993 | Scholl |
| 5,342,881 A | 8/1994 | Muller et al. |
| 5,386,054 A | 1/1995 | Scholl et al. |
| 6,291,577 B1 | 9/2001 | Yang et al. |
| 2008/0257214 A1 | 10/2008 | Bernard et al. |
| 2013/0109793 A1 | 5/2013 | Schaefer et al. |

FOREIGN PATENT DOCUMENTS

| | | | |
|---|---|---|---|
| CN | 1183791 A | 6/1998 | |
| CN | 1273980 A | 11/2000 | |
| CN | 101708994 A | 5/2010 | |
| CN | 101805304 A | 8/2010 | |
| CN | 102356105 A | 2/2012 | |
| CN | 106459339 A | 2/2017 | |
| CN | 112940222 A | 6/2021 | |
| DE | 124590 | 10/1901 | |
| DE | 100 13 186 A1 | 9/2001 | |
| DE | 100 13 187 A1 | 10/2001 | |
| EP | 0 086 871 A2 | 8/1983 | |
| EP | 0 126 299 A1 | 11/1984 | |
| EP | 0 126 300 A1 | 11/1984 | |
| EP | 0 203 874 A1 | 12/1986 | |
| EP | 0 355 443 A2 | 2/1990 | |
| EP | 0 515 933 A2 | 12/1992 | |
| EP | 0 524 507 A1 | 1/1993 | |
| JP | 2000-7910 A * | 1/2000 | |
| JP | 2004-26962 A * | 1/2004 | |
| JP | 4178370 B2 | 11/2008 | |
| JP | 2016-150922 A | 8/2016 | |
| WO | WO-2005089085 A2 * | 9/2005 | ........... C09D 175/04 |
| WO | WO 2008/068198 A1 | 6/2008 | |
| WO | WO 2008/116893 A1 | 10/2008 | |
| WO | WO 2008/116894 A1 | 10/2008 | |
| WO | WO 2008/116895 A1 | 10/2008 | |
| WO | WO 2013/060809 A2 | 5/2013 | |
| WO | WO-2013060809 A2 * | 5/2013 | ........... C07C 263/18 |

OTHER PUBLICATIONS

U.S. Appl. No. 16/621,879, filed Dec. 12, 2019, Harald Schaefer.
U.S. Appl. No. 16/339,124, filed Apr. 3, 2019, Harald Schaefer.
U.S. Appl. No. 16/339,544, filed Apr. 4, 2019, Harald Schaefer.
U.S. Appl. No. 16/647,792, filed Mar. 16, 2020, Harald Schaefer.
International Search Report dated Dec. 11, 2018 in PCT/EP2018/074385 filed Sep. 11, 2018, 2 pages.

(Continued)

*Primary Examiner* — Rabon A Sergent
(74) *Attorney, Agent, or Firm* — Faegre Drinker Biddle & Reath LLP

(57) ABSTRACT

The present invention relates to a new process for preparing polyisocyanates containing isocyanurate groups and being flocculation-stable in solvents from (cyclo)aliphatic diisocyanates.

10 Claims, No Drawings

(56) References Cited

OTHER PUBLICATIONS

European Search Report dated Mar. 15, 2018 in corresponding European Patent Application No. 17192030.9 (with English Translation of Category of Cited Documents), 4 pages.
International Preliminary Report on Patentability and Written Opinion dated Mar. 24, 2020 in PCT/EP2018/074385 (English Translation only), 8 pages.
Liang LinJiao, "The Synthesis of Water-Dispersible Polyisocyanate and Its Study on Coating Performance", Dissertation submitted for the degree of master, South China University of Technology, Mar. 2017, 73 pages.

* cited by examiner

METHOD FOR PRODUCING POLYISOCYANATES OF (CYCLO)ALIPHATIC DIISOCYANATES WHICH ARE FLOCCULATION-STABLE IN SOLVENTS

The present invention relates to a new process for preparing polyisocyanates which are flocculation-stable in solvents from (cyclo)aliphatic diisocyanates.

Flocculation in the sense of this patent refers comprehensively to formation of solids in such a way as to be visible to the naked eye. It ranges from slight hazing, fine precipitates which eddy only as a result of rotating movement about the longitudinal axis of the storage vessel, to the formation of suspended flocs and severe precipitates.

Para-toluenesulfonyl isocyanate $(H_3C(C_6H_4)SO_2$—NCO) and triethyl orthoformate are literature examples of water scavengers which are used in polyisocyanates for stabilization. This stabilization encompasses among other things the prevention of flocculation of aliphatic polyisocyanates in diluted form in solvents as are used for coatings applications. Water-scavenging reactive compounds react with water instead of the isocyanate groups and prevent the polyisocyanates from being hydrolyzed to form amines, and these amines from reacting with further polyisocyanate to form high-functionality (poly)urea polyisocyanates. The latter polyisocyanates have a poor solubility in polyisocyanates and their solutions, and flocs and precipitates may form.

A disadvantage of water scavengers is that they have to be added (at least) stoichiometrically to the amount of water which is present or is anticipated. In the case of para-toluenesulfonyl isocyanate, this corresponds to 12 times the amount by weight of water, and in the case of triethyl orthoformate to 9 times the amount. In the case of para-toluenesulfonyl isocyanate, manufacturers in fact recommend twice the equivalent amount relative to water, respective amounts of para-toluenesulfonyl isocyanate of 0.5-4.0% and 1-3% of triethyl orthoformate, based on the total weight of the formulation. Where such amounts are used, they have the effect, as a result of the dilution factor alone, of reducing the NCO groups accordingly, and this is deleterious for the coatings properties. Para-toluenesulfonyl isocyanate reacts to form a sulfonamide and carbon dioxide, possibly with a build-up of pressure in the storage vessel.

DE 124590 describes the application of sulfonyl isocyanates as water-binding components in polyurethane prepolymers. EP 86871 describes disadvantages of these compounds, since the pronounced crystallization tendency of the tosylamide formed by reaction with water leads to bittiness in the coating material. Moreover, the tosyl isocyanate is so highly reactive that it reacts extremely vigorously with water.

JP4178370 B2 describes a solution consisting of an NCO-terminated urethane prepolymer, especially based on toluene diisocyanate, a silyl phosphate and/or phosphonate, and solvent, and also an adhesive or a paint using the solution.

The examples specifically describe three toluene diisocyanate-, one methylenediphenyl-, and one hexamethylene diisocyanate-based prepolymer.

U.S. Pat. No. 6,291,577 discloses a method for scavenging moisture in polyisocyanate formulations by admixing the polyisocyanate formulation with water scavengers comprising a) di-tert-butylhydroxytoluene selected from the group of 2,6-di-tert-butylhydroxytoluene and 2-tert-butylhydroxytoluene and b) alkyl esters of toluenesulfonic acid with an at least 90% fraction of para-alkyl esters, optionally in at least one solvent. Stated by way of example is a package of moisture scavengers consisting of 0.19% bis(tert-butyl)hydroxytoluene (BHT) and 1.0% methyl para-toluenesulfonate, optionally in combination with other moisture scavengers, relative to a polyisocyanate containing isocyanurate groups and based on hexamethylene diisocyanate, as a 40% strength solution in n-butyl acetate. Corresponding mixtures are stable on storage for 11 weeks without hazing or yellowing. A disadvantage of the method is that the amounts of moisture scavengers are very high, meaning that the NCO value of the polyisocyanate is reduced by 1% by dilution by the moisture scavenger package. The solubility of methyl para-toluenesulfonate is poor. At room temperature, for example, it does dissolve 1% in butyl acetate, but not in 10% strength form.

US 2008/0257214 describes the use of certain trimethylsilyl-containing compounds such as bistrimethylsilylacetamide or hexamethyldisilazane as water scavengers for preventing instances of hazing and formation of carbon dioxide by polyisocyanates in solvents. As with the majority of drying agents, these compounds have to be added at least stoichiometrically. The cleavage products formed consume NCO groups.

EP 203,874 discloses trialkyl-chloro-tin compounds for stabilizing polyisocyanates in organic solvents against floc. Triorgano-tin compounds are highly toxic.

WO 2013060809 describes the use of additives selected from the group consisting of a1) organic acids having a pKa of below 4.2, selected from the group consisting of ala) aromatic sulfonic acids and a1b) singularly or doubly alkoxy-, mercapto- or alkylmercapto-substituted alkanecarboxylic acids having two carbon atoms, singularly or doubly halogen-, alkoxy-, mercapto- or alkyl-mercapto-substituted alkanecarboxylic acids, alkenedicarboxylic acids or alkanedicarboxylic acids having at least three carbon atoms, a2) phosphites of the formula

where R is preferably an aryl group which is substituted in positions 2, 4 and 6 as follows:
Position 2: tert-butyl, tert-amyl,
Position 4: hydrogen, alkyl, tert-butyl or tert-amyl, and
Position 6: hydrogen, alkyl, tert-butyl or tert-amyl,
with the proviso that at least one of the substituents in positions 4 and 6 is not hydrogen, a3) phosphonites of the formula $(RO)_2P$—X—$P(RO)_2$
where R is preferably an aryl group which is substituted in positions 2, 4 and 6 as follows:
Position 2: tert-butyl, tert-amyl,
Position 4: hydrogen, alkyl, tert-butyl or tert-amyl, and
Position 6: hydrogen, alkyl, tert-butyl or tert-amyl,
with the proviso that at least one of the substituents in positions 4 and 6 is not hydrogen, and X in this case is an arylene group, a4) acidic phosphorus derivatives selected from the group consisting of a4a) mono- and di-$C_1$ to $C_{12}$ alkyl phosphates, a4b) mono- and di-$C_1$ to $C_{12}$ alkyl phosphonates, a4c) mono-$C_1$ to $C_{12}$ alkyl phosphinates, and a4d) alkyl derivatives of phosphorus-containing diacids, a5) blocked aromatic sulfonic acids for reducing flocculation and/or precipitation in polyisocyanate mixtures which comprise at least one solvent.

A disadvantage is that the flocculation stability of these mixtures on storage is still not sufficient, and hence there continues to be a need for improved stabilization.

One specific problem arises, for example, for refinish applications (automotive refinish), where long storage times of the products in small containers are a given. Manufacturers of the polyisocyanate component in solvent provide their customers with guarantees of the retention of the product properties for, for example, six months. Storage at the premises of the manufacturer, storage in the course of global transport, or storage of excess by the customer prolong these periods. As a result of low-volume containers and/or repeated opening of these containers, ambient moisture comes into contact with the polyisocyanate component. The solvents used likewise comprise traces of moisture. Storage effects are exacerbated, particularly in countries in Southeast Asia, by high atmospheric humidity and high storage temperatures.

The same problems can be assumed generally in all applications involving prolonged storage times, particularly in relatively small containers, as for example in many industrial applications.

It was an object of the present invention to provide a method with which polyisocyanates during storage in solvents on exposure to (atmospheric) moisture exhibit a higher flocculation stability in storage, and the additives have to be added in the smallest possible amount.

The object has been achieved through the use of additives for reducing flocculation and/or precipitation in polyisocyanate mixtures which comprise at least one solvent (C) and at least one polyisocyanate (A),
where the additives are selected from the group of silyl esters (B) consisting of silyl phosphates and silyl phosphonates and are used in an amount of 1 to 250 ppm by weight based on the at least one polyisocyanate (A).

Polyisocyanates (A) for the purposes of the invention are polyisocyanates in their as-synthesized form, and mixtures of these polyisocyanates.

They include the compounds described in more detail below.

The monomeric isocyanates used for preparing the polyisocyanates may be aromatic, aliphatic or cycloaliphatic, preferably aliphatic or cycloaliphatic, as referred to in abbreviated form in this specification as (cyclo)aliphatic; aliphatic isocyanates are particularly preferred.

Aromatic isocyanates are those which comprise at least one aromatic ring system, thus including both purely aromatic and also araliphatic compounds.

Cycloaliphatic isocyanates are those which comprise at least one cycloaliphatic ring system. Aliphatic isocyanates are those which comprise exclusively linear or branched chains, i.e., acyclic compounds.

The monomeric isocyanates are preferably diisocyanates, which carry precisely two isocyanate groups. They can, however, in principle also be monoisocyanates, having one isocyanate group.

In principle, higher isocyanates having on average more than 2 isocyanate groups are also contemplated. Suitability therefor is possessed for example by triisocyanates such as triisocyanatononane, 2'-isocyanatoethyl (2,6-diisocyanatohexanoate), 2,4,6-triisocyanato-toluene, triphenylmethane triisocyanate or 2,4,4'-triisocyanatodiphenyl ether, or the mixtures of diisocyanates, triisocyanates, and higher polyisocyanates that are obtained, for example, by phosgenation of corresponding aniline/formaldehyde condensates and represent methylene-bridged polyphenyl polyisocyanates, more particularly triisocyanatononane and 2'-isocyanatoethyl-(2,6-diisocyanatohexanoate).

The monomeric isocyanates are preferably isocyanates having 4 to 20 C atoms. Examples of typical diisocyanates are aliphatic diisocyanates such as tetramethylene diisocyanate, pentamethylene 1,5-diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, (e.g., methyl 2,6-diisocyanatohexanoate or ethyl 2,6-diisocyanatohexanoate) trimethylhexane diisocyanate or tetramethylhexane diisocyanate, cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane or 2,4-, or 2,6-diisocyanato-1-methylcyclohexane, and also 3 (or 4), 8 (or 9)-bis(isocyanatomethyl)tricyclo[5.2.1.0$^{2,6}$]decane isomer mixtures, and also aromatic diisocyanates such as tolylene 2,4- or 2,6-diisocyanate and the isomer mixtures thereof, m- or p-xylylene diisocyanate, 2,4'- or 4,4'-diisocyanatodiphenylmethane and the isomer mixtures thereof, phenylene 1,3- or 1,4-diisocyanate, 1-chlorophenylene 2,4-diisocyanate, naphthylene 1,5-diisocyanate, diphenylene 4,4'-diisocyanate, 4,4'-diisocyanato-3,3'-dimethylbiphenyl, 3-methyldiphenylmethane 4,4'-diisocyanate, tetramethylxylylene diisocyanate, 1,4-diisocyanatobenzene or diphenyl ether 4,4'-diisocyanate.

Particular preference is given to hexamethylene 1,6-diisocyanate, pentamethylene 1,5-diisocyanate, 1,3-bis(isocyanatomethyl)cyclohexane, isophorone diisocyanate, and 4,4'- or 2,4'-di(isocyanatocyclohexyl)methane, very particular preference to isophorone diisocyanate and hexamethylene 1,6-diisocyanate, and special preference to hexamethylene 1,6-diisocyanate.

Mixtures of said isocyanates may also be present.

Isophorone diisocyanate is usually in the form of a mixture, specifically a mixture of the cis and trans isomers, generally in a proportion of about 60:40 to 90:10 (w/w), preferably in a proportion of 70:30 to 90:10.

Dicyclohexylmethane 4,4'-diisocyanate may likewise be in the form of a mixture of the different cis and trans isomers.

For the present invention it is possible to use not only those diisocyanates obtained by phosgenating the corresponding amines but also those prepared without the use of phosgene, i.e., by phosgene-free processes. According to EP-A-0 126 299 (U.S. Pat. No. 4,596,678), EP-A-126 300 (U.S. Pat. No. 4,596,679), and EP-A-355 443 (U.S. Pat. No. 5,087,739), for example, (cyclo)aliphatic diisocyanates, such as hexamethylene 1,6-diisocyanate (HDI), isomeric aliphatic diisocyanates having 6 carbon atoms in the alkylene radical, 4,4'- or 2,4'-di(isocyanatocyclohexyl)methane, and 1-isocyanato-3-isocyanatomethyl-3,5,5-trimethylcyclohexane (isophorone diisocyanate or IPDI) can be prepared by reacting the (cyclo)aliphatic diamines with, for example, urea and alcohols to give (cyclo)aliphatic biscarbamic esters and subjecting said esters to thermal cleavage into the corresponding diisocyanates and alcohols. The synthesis takes place usually continuously in a circulation process and in the presence, optionally, of N-unsubstituted carbamic esters, dialkyl carbonates, and other by-products recycled from the reaction process. Diisocyanates obtained in this way generally contain a very low or even unmeasurable fraction of chlorinated compounds, which is advantageous, for example, in applications in the electronics industry.

In one embodiment of the present invention the isocyanates used have a hydrolyzable chlorine content of less than 100 ppm by weight, preferably of less than 50 ppm by weight, more preferably less than 30 ppm, especially less than 20 ppm by weight. This can be measured by means, for example, of ASTM specification D4663-98. The amounts of total chlorine are for example below 1000 ppm by weight, preferably below 800 ppm by weight, and more preferably below 500 ppm by weight (determined by argentometric titration after hydrolysis).

It will be appreciated that it is also possible to employ mixtures of those monomeric isocyanates which have been obtained by reacting the (cyclo)aliphatic diamines with, for example, urea and alcohols and cleaving the resulting (cyclo)aliphatic biscarbamic esters, with those diisocyanates which have been obtained by phosgenating the corresponding amines.

The polyisocyanates (A) which can be formed by oligomerizing the monomeric isocyanates are generally characterized as follows:

The average NCO functionality of such compounds is in general at least 1.8 and can be up to 8, preferably 2 to 5, and more preferably 2.4 to 4.

The isocyanate group content after oligomerization, calculated as NCO=42 g/mol, is preferably at least 15% by weight, more preferably at least 20% by weight. Most preferably, the isocyanate group content after oligomerization is at least 20% by weight and at most 30% by weight.

The polyisocyanates (A) are preferably compounds as follows:

1) Polyisocyanates containing isocyanurate groups and derived from aliphatic and/or cycloaliphatic diisocyanates. Particular preference is given in this context to diisocyanates based on hexamethylene diisocyanate and isophorone diisocyanate. The isocyanurates present are, in particular, trisisocyanatoalkyl and/or trisisocyanatocycloalkyl isocyanurates, which constitute cyclic trimers of the diisocyanates, or respectively are mixtures with their higher homologs containing more than one isocyanurate ring. The isocyanatoisocyanurates generally have an NCO content of 15% to 30% by weight, in particular 15% to 25% by weight, and an average NCO functionality of 2.6 to 8. The polyisocyanates containing isocyanurate groups may to a more minor extent also comprise allophanate groups and/or urethane groups, preferably with a bound alcohol content of less than 2% based on the polyisocyanate.

2) Polyisocyanates containing uretdione groups and having aliphatically and/or cycloaliphatically attached isocyanate groups, in particular those derived from hexamethylene diisocyanate or isophorone diisocyanate. Uretdione diisocyanates are cyclic dimerization products of diisocyanates.

The polyisocyanates containing uretdione groups are frequently obtained as a mixture with other polyisocyanates, more particularly those specified under 1). Polyisocyanates containing uretdione groups typically have functionalities of 2 to 3.

This also includes uretdione/isocyanurate mixtures of any desired composition, more particularly having a monomeric uretdione (dimer) content of 1-40%, in particular 3-15%, more particularly 5-10%.

For this purpose the diisocyanates can be reacted under reaction conditions under which not only uretdione groups but also the other polyisocyanates are formed, or the uretdione groups are formed first of all and are subsequently reacted to give the other polyisocyanates, or the diisocyanates are first reacted to give the other polyisocyanates, which are subsequently reacted to give products containing uretdione groups.

3) Polyisocyanates containing biuret groups and having cycloaliphatically or aliphatically attached isocyanate groups, especially tris(6-isocyanatohexyl)biuret or respectively its mixtures with its higher homologs. These polyisocyanates containing biuret groups generally have an NCO content of 18% to 24% by weight and an average NCO functionality of 2.8 to 6.

4) Polyisocyanates containing allophanate and/or urethane groups and having aliphatically or cycloaliphatically attached isocyanate groups, such as may be obtained, for example, by reacting excess amounts of diisocyanate, such as of hexamethylene diisocyanate, of pentamethylene diisocyanate or of isophorone diisocyanate, with mono- or polyhydric alcohols. These polyisocyanates containing allophanate and/or urethane groups generally have an NCO content of 15% to 24% by weight and an average NCO functionality of 2.0 to 4.5. Polyisocyanates of this kind containing allophanate and/or urethane groups may be prepared without catalyst or, preferably, in the presence of catalysts, such as ammonium carboxylates or ammonium hydroxides, for example, or allophanatization catalysts, such as bismuth, cobalt, cesium, Zn(II) or Zr(IV) compounds, for example, in each case in the presence of monohydric, dihydric or polyhydric, preferably monohydric, alcohols.

These polyisocyanates containing allophanate groups and/or urethane groups frequently occur in mixed forms with the polyisocyanates identified under 1).

5) Polyisocyanates comprising iminooxadiazinedione groups, derived preferably from hexamethylene diisocyanate, pentamethylene diisocyanate or isophorone diisocyanate. Polyisocyanates of this kind comprising iminooxadiazinedione groups are preparable from diisocyanates by means of specific catalysts, e.g., phosphonium hydrogen difluoride.

6) Hyperbranched polyisocyanates, of the kind known for example from DE-A1 10013186 or DE-A1 10013187.

7) The polyisocyanates mentioned can be converted, following their preparation, into polyisocyanates containing biuret groups or allophanate/urethane groups and having cycloaliphatically or aliphatically attached isocyanate groups. The formation of biuret groups, for example, is accomplished by addition of water or by reaction with amines. The formation of allophanate and/or urethane groups is accomplished by reaction with monohydric, dihydric or polyhydric, preferably monohydric, alcohols, in the presence if desired of suitable catalysts. These polyisocyanates containing biuret or allophanate/urethane groups generally have an NCO content of 15% to 25% by weight and an average NCO functionality of 3 to 8.

8) Modified polyisocyanates for dual cure applications, i.e., polyisocyanates which as well as the groups described under 1)-7) also comprise groups resulting formally from addition of molecules containing NCO-reactive groups and UV-crosslinkable or actinic-radiation-crosslinkable groups to the isocyanate groups of the above molecules. These molecules are, for example, hydroxyalkyl (meth) acrylates and other hydroxyvinyl compounds.

The diisocyanates or polyisocyanates recited above may also be present at least partly in blocked form.

Classes of compounds used for blocking are described in D. A. Wicks, Z. W. Wicks, Progress in Organic Coatings, 36, 148-172 (1999), 41, 1-83 (2001) and also 43, 131-140 (2001).

Examples of classes of compounds used for blocking are phenols, imidazoles, triazoles, pyrazoles, oximes, N-hydroxyimides, hydroxybenzoic esters, secondary amines, lactams, CH-acidic cyclic ketones, malonic esters or alkyl acetoacetates.

In one preferred embodiment of the present invention the polyisocyanate (A) is selected from the group consisting of isocyanurates, iminooxadiazinediones, biurets, urethanes, and allophanates, preferably from the group consisting of isocyanurates, urethanes, and allophanates; more preferably it is a polyisocyanate containing isocyanurate groups.

In one particularly preferred embodiment the polyisocyanate (A) encompasses polyisocyanates comprising isocyanurate groups and obtained from 1,6-hexamethylene diisocyanate.

In one further preferred embodiment the polyisocyanate (A) encompasses a mixture of polyisocyanates comprising isocyanurate groups and obtained very preferably from 1,6-hexamethylene diisocyanate and from isophorone diisocyanate.

In one particularly preferred embodiment the polyisocyanate (A) is a polyisocyanate comprising predominantly isocyanurate groups, having a viscosity of 500-4000 mPa*s, and/or a low-viscosity allophanate optionally comprising isocyanurate and/or urethane, having a viscosity of 150-1600 mPa*s.

In this specification, unless noted otherwise, the viscosity is reported at 23° C. in accordance with DIN EN ISO 3219/A.3 in a cone/plate system with a shear rate of 1000 s$^{-1}$.

The process for preparing the polyisocyanates (A) may take place as described in WO 2008/68198, particularly from page 20, line 21 to page 27, line 15 therein, as is hereby made part of the present specification by reference.

The reaction may be terminated, for example, as described therein from page 31, page 19 to page 31, line 31, and the product may be worked up as described therein from page 31, line 33 to page 32, line 40, as is hereby made part of the present specification in each case by reference.

The reaction may alternatively and preferably take place as described in WO 2005/087828 for ammonium alpha-hydroxycarboxylate catalysts. The reaction may be terminated, for example as described therein from page 11, line 12 to page 12, line 5, as is hereby made part of the present specification by reference.

The reaction may alternatively take place as described in CN 10178994A or CN 101805304.

In the case of thermally unstable catalysts it is also possible, moreover, to terminate the reaction by heating the reaction mixture to a temperature above at least 80° C., preferably at least 100° C., more preferably at least 120° C. In general the heating of the reaction mixture as required to remove the unreacted isocyanate by distillation in the work-up procedure is sufficient for this purpose.

Both for thermally stable and thermally unstable catalysts, the possibility exists of terminating the reaction at relatively low temperatures by adding deactivators. Examples of suitable deactivators include hydrogen chloride, phosphoric acid, organic phosphates, such as dibutyl phosphate or diethylhexyl phosphate, and carbamates such as hydroxyalkyl carbamate.

These compounds are added neat or diluted in suitable concentration needed for termination of reaction.

Additives with inventive antiflocculating effect are: silyl esters (B) selected from the group of silyl phosphates and silyl phosphonates.

Preferred silyl esters (B) are the following compounds:

(I)

(II)

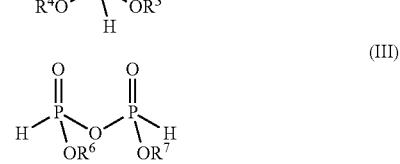

(III)

In these formulae the radicals $R^1$ to $R^7$, each independently of one another, are trialkylsilyl group, alkyl group or hydrogen, and each compound must comprise at least one trialkylsilyl group. The radicals $R^1$ to $R^7$ are preferably each trialkylsilyl groups or alkyl groups, and each compound must comprise at least one trialkylsilyl group. More preferably all of the radicals $R^1$ to $R^7$ are trialkylsilyl groups.

The alkyl groups, and the alkyl groups of the trialkylsilyl groups, are preferably $C_1$ to $C_{18}$ alkyl groups.

The alkyl groups of the trialkylsilyl groups are preferably identical.

The alkyl groups of the trialkylsilyl groups are preferably methyl and/or ethyl, more preferably methyl.

Tris(trimethylsilyl)phosphoric acid is the particularly preferred species.

Particularly preferred silyl esters (B) are silyl phosphates, especially preferably tris(silyl) phosphate, very preferably tris(trimethylsilyl) phosphate.

The silyl esters (B) are added in amounts, based on the polyisocyanate (A), of 1 to 250 ppm by weight, preferably of 5 to 250 ppm by weight, more preferably of 10 to 200 ppm by weight, very preferably 10 to 150 ppm by weight.

The silyl ester (B) is preferably used substoichiometrically in relation to the amount of water present in the polyisocyanate mixture.

Solvents (C) which can be used for the polyisocyanate component, and also for the binder components and any further components, are those which do not have any groups reactive toward isocyanate groups or toward blocked isocyanate groups, and in which the polyisocyanates are soluble to an extent of at least 10%, preferably at least 25%, more preferably at least 50%, very preferably at least 75%, more particularly at least 90%, and especially at least 95% by weight.

Examples of solvents of this kind are aromatic hydrocarbons (including alkylated benzenes and naphthalenes) and/or (cyclo)aliphatic hydrocarbons and mixtures thereof, ketones, esters, ether esters, alkoxylated alkyl alkanoates, ethers, and mixtures of the solvents.

Preferred aromatic hydrocarbon mixtures are those which comprise predominantly aromatic $C_7$ to $C_{14}$ hydrocarbons and may encompass a boiling range from 110 to 300° C.; particular preference is given to toluene, o-, m- or p-xylene, trimethylbenzene isomers, tetramethylbenzene isomers, ethylbenzene, cumene, tetrahydronaphthalene; and mixtures comprising them.

Examples thereof are the Solvesso® products from ExxonMobil Chemical, especially Solvesso® 100 (CAS No. 64742-95-6, predominantly $C_9$ and $C_{10}$ aromatics, boiling range about 154-178° C.), 150 (boiling range about 182-207° C.), and 200 (CAS No. 64742-94-5), and also the Shellsol® products from Shell, Caromax® (e.g., Caromax® 18) from Petrochem Carless and Hydrosol from DHC (e.g., as Hydrosol® A 170). Hydrocarbon mixtures comprising paraffins, cycloparaffins, and aromatics are also available commercially under the names Kristalloel (for example, Kristalloel 30, boiling range about 158-198° C. or Kristalloel 60: CAS No. 64742-82-1), white spirit (for example likewise CAS No. 64742-82-1) or solvent naphtha (light: boiling range about 155-180° C., heavy: boiling range about 225-300° C.). The aromatics content of such hydrocarbon mixtures is generally more than 90%, preferably more than 95%, more preferably more than 98%, and very preferably more than 99% by weight. It may be useful to use hydrocarbon mixtures having a particularly reduced naphthalene content.

Examples of (cyclo)aliphatic hydrocarbons include decalin, alkylated decalin, and isomer mixtures of linear or branched alkanes and/or cycloalkanes.

The amount of aliphatic hydrocarbons is generally less than 5%, preferably less than 2.5%, and more preferably less than 1% by weight.

Esters are, for example, n-butyl acetate, ethyl acetate, 1-methoxyprop-2-yl acetate, and 2-methoxyethyl acetate.

Ethers are, for example, THF, dioxane, and also the dimethyl, diethyl or di-n-butyl ethers of ethylene glycol, diethylene glycol, triethylene glycol, propylene glycol, dipropylene glycol or tripropylene glycol.

Ketones are, for example, acetone, diethyl ketone, ethyl methyl ketone, isobutyl methyl ketone, methyl amyl ketone, and tert-butyl methyl ketone.

Ether esters are, for example, ethyl ethoxypropionate EEP, methoxymethyl acetate, butoxyethyl acetate BGA, ethoxy-1-methylethyl acetate, methoxy-1-methylethyl acetate.

Preferred solvents (C) are xylene, n-butyl acetate, ethyl acetate, 1-methoxyprop-2-yl acetate, 2-methoxyethyl acetate, and mixtures thereof, especially with the aromatic hydrocarbon mixtures recited above, more particularly xylene and Solvesso® 100.

Mixtures of this kind can be made in a volume ratio of 5:1 to 1:5, preferably in a volume ratio of 4:1 to 1:4, more preferably in a volume ratio of 3:1 to 1:3, and very preferably in a volume ratio of 2:1 to 1:2.

Preferred examples are butyl acetate/xylene, methoxypropyl acetate/xylene 1:1, butyl acetate/solvent naphtha 100 1:1, butyl acetate/Solvesso® 100 1:2, and Kristalloel 30/Shellsol® A 3:1.

Particular preference is given to butyl acetate, 1-methoxyprop-2-yl acetate, methyl amyl ketone, xylene, and Solvesso® 100.

The additives with antiflocculant effect are preferably dispersed homogeneously, preferably using mixing devices.

The additives with antiflocculant defect can be added in a variety of ways—for example, as they are, in solvents (C) and/or other additives, including, in particular, in other solvents, in which there should preferably be good solubility, such as, for example, dialkyldicarboxylic esters such as dioctyladipic ester and dinonyladipic ester, phosphoric acid trialkyl esters, phthalic esters and ring-hydrogenated phthalic esters, such as diisononyl cyclohexane-1,2-dicarboxylate, for example, or in alcohols. Aromatic diesters are less preferred.

The additives with antiflocculant effect may be introduced, for example, into the pure polyisocyanate, into a saleable polyisocyanate in solvent, in a polyisocyanate component, consisting, for example, of polyisocyanate, solvent(s), and additives. A saleable polyisocyanate component of this kind may be used with a corresponding polyol component without further additions, optionally after separate storage, by blending the two components for coating.

Preference is given to additives which are present in liquid form or which can be incorporated by stirring with low and short-term shearing forces.

The additives with antiflocculant effect can be added to the polyisocyanate at elevated temperature directly after the distillation at from about 170° C. to the ambient temperature, in the case of solid additives preferably at a temperature above their melting point, or else in solid form, in which case the homogenization effort becomes higher.

In one specific form they are mixed batchwise, optionally in solvent, with the polyisocyanate in less than an hour at between room temperature and 70° C. in a stirred tank.

In another specific form they are added, optionally in solvent, continuously in a static mixer at between room temperature and 70° C. Temperatures below 35° C. are preferred, more particularly at room temperature.

Preliminary dissolution in solvent may be useful in particular in the case of solid additives with antiflocculant effect, with in some cases high melting points and poor solubilities in polyisocyanate and solvent.

Another form of use is the preparation of a stock solution, for example, in solvent, additive mixtures and/or polyisocyanate.

In the examples given below, the amounts in which the antiflocculants are added are typically significantly substoichiometric in relation to the total amount of water in the mixture, or respectively in polyisocyanate components for coatings application which may optionally also comprise additional amounts of solvent.

In one preferred form it is advantageous, for the reasons given above and further reasons, to add to the polyisocyanate the minimum amount of additive necessary to adequately prevent flocculation for, for example, six months. Further reasons for specifying a minimally necessary amount are that many of the additives may have further functional effect in polyurethane systems. The additives could interact with Lewis acid catalysts or with basic additives such as UV stabilizers or amine catalysts and thereupon form highly soluble salts or prevent the action of additives. It is therefore advantageous to minimize the amount of additive, and to make a selective choice optionally in dependence on other additives.

Frequently it is the case that the flocculation tendency goes up with increasing dilution by the solvent, particularly at solvent contents of more than 50%, more particularly at more than 60%.

Additionally, the polyisocyanate mixture admixed with additive may optionally comprise a urethanization catalyst. This catalyst may be, for example, an amine or an organometallic compound.

Said catalyst is preferably a Lewis acid.

Amine catalysts are, for example, trifunctional cycloaliphatic or aromatic amines with oxygen in the heterocycle. Examples thereof are N-methylmorpholine, N-methylpiperidine, pyrrolidine, quinuclidine or 1,4-diazabicyclo[2.2.2]octane, diazabicycloundecane.

Examples of organometallic compounds include tin(IV) and tin(II) salts of organic carboxylic acids, e.g., tin(II) diacetate, tin(II) dioctoate, tin(II) bis(ethylhexanoate), and tin(II) dilaurate. It is also possible to use zinc(II) salts, such as zinc(II) dioctoate, dineooctanoate, diacetate, or oxalate, for example. Metal complexes are also possible, such as acetylacetonates of iron, of titanium, of aluminum, of zirconium, of manganese, of nickel, of zinc, and of cobalt. Other metal catalysts are described by Blank et al. in Progress in Organic Coatings, 1999, vol. 35, pages 19-29.

Dialkytin(IV) salts of organic carboxylic acids are, for example, dimethyltin diacetate, dibutyltin diacetate, dibutyltin dibutyrate, dibutyltin bis(2-ethylhexanoate), dibutyltin dilaurate, dibutyltin maleate, dioctyltin dilaurate, and dioctyltin diacetate. Preference is given to dibutyltin diacetate and dibutyltin dilaurate. For toxicological reasons, tin salts are less preferred, but are still frequently used in practice.

Other preferred Lewis-acidic organometallic compounds are zinc(II) dioctoate, zirconium acetylacetonate, and zirconium 2,2,6,6-tetramethyl-3,5-heptanedionate.

Bismuth and cobalt catalysts, cerium salts such as cerium octoates, and cesium salts can also be used as catalysts.

Bismuth catalysts are more particularly bismuth carboxylates, especially bismuth octoates, ethylhexanoates, neodecanoates or pivalates; examples are K-KAT 348 and XK-601 from King Industries, TIB KAT 716, 716LA, 716XLA, 718, 720, 789 from TIB Chemicals, and those from Shepherd Lausanne, and also catalyst mixtures of, for example, bismuth organyls and zinc organyls.

Cesium salts contemplated include those compounds in which the following anions are used: $F^-$, $Cl^-$, $ClO^-$, $ClO_3^-$, $ClO_4^-$, $Br^-$, $I^-$, $IO_3^-$, $CN^-$, $OCN^-$, $NO_2^-$, $NO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^-$, $H_2PO_2^-$, $H_2PO_4^-$, $HPO_4^{2-}$, $PO_4^{3-}$, $P_2O_7^{4-}$, $(OC_nH_{2n+1})^-$, $(C_nH_{2n-1}O_2)^-$, $(C_nH_{2n-3}O_2)^-$, and $(C_{n+1}H_{2n-2}O_4)^{2-}$, where n stands for the numbers 1 to 20. Preference here is given to cesium carboxylates in which the anion conforms to the formulae $(C_nH_{2n-1}O_2)^-$ and also $(C_{n+1}H_{2n-2}O_4)^{2-}$ with n as 1 to 20. Particularly preferred cesium salts have monocarboxylate anions of the general formula $(C_nH_{2n-1}O_2)^-$, where n stands for the numbers 1 to 20. Particularly noteworthy in this context are formate, acetate, propionate, hexanoate, and 2-ethylhexanoate.

As further, typical coatings components and/or additives it is possible for example to make use of the following: stabilizers, UV stabilizers such as UV absorbers and suitable free-radical scavengers (more particularly HALS compounds—hindered amine light stabilizers), activators (accelerants), driers, extenders, pigments, dyes, antistatic agents, flame retardants, thickeners, thixotropic agents, surface-active agents, viscosity modifiers, plasticizers or chelating agents. Preference is given to UV stabilizers.

Stabilizers are at least one compound with stabilizing effect, "stabilizing" denoting the capacity to reduce the development of a color number and/or of the viscosity of the polyisocyanate in the course of storage over a certain time period relative to those corresponding mixtures which comprise no compounds with stabilizing effect.

Stabilization may relate either to the polyisocyanate alone or else to premixes of the polyisocyanates with further, typical coatings components and/or additives, optionally with addition of other components. This includes, in one particular embodiment, the storage of one of these compounds prior to actual application of the coating material.

These compounds with stabilizing effect are preferably selected from the group consisting of primary antioxidants (free-radical scavengers), secondary antioxidants (compounds which prevent radicals being formed, more particularly by scavenging and/or decomposing peroxides), and acidic stabilizers (Brønsted acids).

The primary antioxidants are preferably sterically hindered phenols. Such sterically hindered phenols are described for example in WO 2008/116894, preferably the compounds described therein from page 14, line 10 to page 16, line 10, hereby incorporated by reference as part of the present disclosure content.

The phenols in question or bridged bisphenols are preferably those which have exactly one phenolic hydroxyl group on the aromatic ring, and more preferably those which have any desired substituent, preferably an alkyl group, in the ortho-positions, very preferably in ortho- and para-position to the phenolic hydroxyl group, more particularly alkyl 3-(3,5-di-tert-butyl-4-hydroxyphenyl)propionates, or substituted alkyl derivatives of such compounds.

In conjunction with additives of the invention they are part of the invention, preferably 2,6-bis-tert-butyl-4-methylphenol (BHT), 3-[3,5-di-tert-butyl-4-hydroxyphenyl]propionic esters in general, pentaerythritol tetrakis(3-(3,5-di-tert-butyl-4-hydroxyphenyl)propionate) (CAS No. 6683-19-8; e.g., Irganox® 1010), 3,3',3'',5,5',5''-hexa-tert-butyl-a,a',a''-(mesitylene-2,4,6-triyl)tri-p-cresol (CAS No. 1709-70-2; e.g., Irganox® 1330), 1,3,5-tris(3,5-di-tert-butyl-4-hydroxybenzyl)-1,3,5-triazine-2,4,6(1H,3H,5H)-trione (CAS No. 27676-62-6; e.g., Irganox® 3114), isooctyl 3-(3,5-ditert-butyl-4-hydroxyphenyl)propionate (CAS No. 146598-26-7, e.g., Irganox® 1135), and octadecyl 3-(3,5-di-tert-butyl-4-hydroxyphenyl)propionate (CAS No. 2082-79-3, e.g., Irganox® 1076).

Particularly preferred are 2,6-di-tert-butyl-4-methylphenol (BHT); isooctyl 3-(3,5-di-tert-butyl-4-hydroxyphenyl)propionate (CAS No. 146598-26-7, e.g., Irganox® 1135), and octadecyl 3-(3,5-di-tert-butyl-4-hydroxyphenyl)propionate (CAS No. 2082-79-3, Irganox® 1076), and pentaerythritol tetrakis(3-(3,5-di-tert-butyl-4-hydroxyphenyl) propionate) (CAS No. 6683-19-8; e.g., Irganox® 1010).

Such phenols may also be constituents of a polyphenolic system with a plurality of phenol groups: pentaerythritol tetrakis(3-(3,5-di-tert-butyl-4-hydroxyphenyl)propionate) (e.g., Irganox® 1010); ethylene bis(oxyethylene)bis(3-(5-tert-butyl-4-hydroxy-m-tolyl)propionate) (e.g., Irganox® 245): 3,3',3'',5,5',5''-hexa-tert-butyl-a,a',a''-(mesitylene-2,4,6-triyl)tri-p-cresol (e.g., Irganox® 1330); 1,3,5-tris(3,5-di-tert-butyl-4-hydroxybenzyl)-1,3,5-triazine-2,4,6(1H,3H,5H)-trione (e.g., Irganox® 3114), in each case products of Ciba Spezialitätenchemie, now BASF SE.

The secondary antioxidants are preferably selected from the group consisting of phosphonites, phosphonates, and thioethers, preferably from phosphonites or phosphonates.

Preferred phosphonites are described in WO 2008/116894, particularly from page 11, line 8 to page 14, line 8, therein, hereby made part of the present disclosure content by reference.

Preferred phosphonates are described in WO 2008/116895, particularly from page 10, line 38 to page 12, line 41, therein, hereby made part of the present disclosure content by reference.

Preferred thioethers are described in WO 2008/116893, particularly from page 11, line 1 to page 15, line 37, therein, hereby made part of the present disclosure content by reference.

The acidic stabilizers are Brønsted acids, as described in WO 2008/116894, particularly from page 17, line 34 to page 18, line 23, therein, hereby made part of the present disclosure content by reference.

Suitable UV absorbers comprise oxanilides, triazines and benzotriazoles (the latter available, for example, as Tinuvin® products from BASF SE) and benzophenones (e.g., Chimassorb® 81 from BASF SE). Preference is given, for example, to 95% benzenepropanoic acid, 3-(2H-benzotriazol-2-yl)-5-(1,1-dimethylethyl)-4-hydroxy-, C7-9-branched and linear alkyl esters; 5% 1-methoxy-2-propyl acetate (e.g., Tinuvin® 384) and α-[3-[3-(2H-benzotriazol-2-yl)-5-(1,1-dimethylethyl)-4-hydroxyphenyl]-1-oxopropyl]-ω-hydroxypoly(oxo-1,2-ethanediyl) (e.g., Tinuvin® 1130), in each case products, for example, of BASF SE. DL-alpha-Tocopherol, tocopherol, cinnamic acid derivatives, and cyanoacrylates can likewise be used for this purpose.

These can be employed alone or together with suitable free-radical scavengers, examples being sterically hindered amines (often also identified as HALS or HAS compounds; hindered amine (light) stabilizers) such as 2,2,6,6-tetramethylpiperidine, 2,6-di-tert-butylpiperidine or derivatives thereof, e.g., bis(2,2,6,6-tetramethyl-4-piperidyl) sebacate. They are obtainable, for example, as Tinuvin® products and Chimassorb® products from BASF SE. Preference in joint use with Lewis acids, however, is given to those hindered amines which are N-alkylated, examples being bis(1,2,2,6,6-pentamethyl-4-piperidinyl) [[3,5-bis(1,1-dimethylethyl)-4-hydroxyphenyl]methyl]butylmalonate (e.g., Tinuvin® 144 from BASF SE); a mixture of bis(1,2,2,6,6-pentamethyl-4-piperidinyl)sebacate and methyl(1,2,2,6,6-pentamethyl-4-piperidinyl) sebacate (e.g., Tinuvin® 292 from BASF SE); or which are N—(O-alkylated), such as, for example, decanedioic acid bis(2,2,6,6-tetramethyl-1-(octyloxy)-4-piperidinyl) ester, reaction products with 1,1-dimethylethyl hydroperoxide and octane (e.g., Tinuvin® 123 from BASF SE) and especially with the HALS triazine 2,4-bis[N-butyl-N-(1-cyclohexyloxy-2,2,6,6-tetramethylpiperidin-4-yl)amino]-6-(2-hydroxyethyl-amine)-1,3,5-triazine (e.g., Tinuvin® 152 from BASF SE). Additives insensitive to acid, such as Tinuvin® 152, are advantageous here.

Drying agents are, for example, para-toluenesulfonyl isocyanate (e.g., Additives TI from Borchers/OMG) and ethyl orthoformate (e.g., Additive OF from Borchers/OMG).

UV stabilizers are used typically in amounts of 0.1% to 5.0% by weight, based on the solid components present in the preparation.

Suitable thickeners include, in addition to free-radically (co)polymerized (co)polymers, typical organic and inorganic thickeners such as hydroxymethylcellulose or bentonite.

Chelating agents which can be used include, for example, ethylenediamineacetic acid and salts thereof and also β-diketones.

Pigments in the true sense are, according to CD Römpp Chemie Lexikon—Version 1.0, Stuttgart/New York: Georg Thieme Verlag 1995, with reference to DIN 55943, particulate "colorants that are organic or inorganic, chromatic or achromatic and are virtually insoluble in the application medium".

Virtually insoluble here means a solubility at 25° C. below 1 g/1000 g application medium, preferably below 0.5, more preferably below 0.25, very particularly preferably below 0.1, and in particular below 0.05 g/1000 g application medium.

Examples of pigments in the true sense comprise any desired systems of absorption pigments and/or effect pigments, preferably absorption pigments. There are no restrictions whatsoever on the number and selection of the pigment components. They may be adapted as desired to the particular requirements, such as the desired perceived color, for example, as described in step a), for example. It is possible for example for the basis to be all the pigment components of a standardized mixer system.

Effect pigments are all pigments which exhibit a platelet-shaped construction and give a surface coating specific decorative color effects. The effect pigments are, for example, all of the pigments which impart effect and can be used typically in vehicle finishing and industrial coatings. Examples of such effect pigments are pure metallic pigments, such as aluminum, iron or copper pigments; interference pigments, such as titanium dioxide-coated mica, iron oxide-coated mica, mixed oxide-coated mica (e.g., with titanium dioxide and $Fe_2O_3$ or titanium dioxide and $Cr_2O_3$), metal oxide-coated aluminum; or liquid-crystal pigments, for example.

The coloring absorption pigments are, for example, typical organic or inorganic absorption pigments that can be used in the coatings industry. Examples of organic absorption pigments are azo pigments, phthalocyanine pigments, quinacridone pigments, and pyrrolopyrrole pigments. Examples of inorganic absorption pigments are iron oxide pigments, titanium dioxide, and carbon black.

Dyes are likewise colorants, and differ from the pigments in their solubility in the application medium; i.e., they have a solubility at 25° C. of more than 1 g/1000 g in the application medium.

Examples of dyes are azo, azine, anthraquinone, acridine, cyanine, oxazine, polymethine, thiazine, and triarylmethane dyes. These dyes may find application as basic or cationic dyes, mordant dyes, direct dyes, disperse dyes, development dyes, vat dyes, metal complex dyes, reactive dyes, acid dyes, sulfur dyes, coupling dyes or substantive dyes.

Coloristically inert fillers are all substances/compounds which on the one hand are coloristically inactive, i.e., exhibit a low intrinsic absorption and have a refractive index similar to that of the coating medium, and which on the other hand are capable of influencing the orientation (parallel alignment) of the effect pigments in the surface coating, i.e., in the applied coating film, and also properties of the coating or of the coating compositions, such as hardness or rheology, for example. Inert substances/compounds which can be used are given by way of example below, but without restricting the concept of coloristically inert, topology-influencing fillers to these examples. Suitable inert fillers meeting the definition may be, for example, transparent or semitransparent fillers or pigments, such as silica gels, blanc fixe, kieselguhr, talc, calcium carbonates, kaolin, barium sulfate, magnesium silicate, aluminum silicate, crystalline silicon dioxide, amorphous silica, aluminum oxide, microspheres or hollow microspheres made, for example, of glass, ceramic or polymers, with sizes of 0.1-50 μm, for example. Additionally as inert fillers it is possible to employ any desired solid inert organic particles, such as urea-formaldehyde condensates, micronized polyolefin wax and micronized amide wax, for example. The inert fillers can in each case also be used in a mixture. It is preferred, however, to use only one filler in each case.

Preferred fillers comprise silicates, examples being silicates obtainable by hydrolysis of silicon tetrachloride, such as Aerosil® from Degussa, siliceous earth, talc, aluminum silicates, magnesium silicates, calcium carbonates, etc.

The polyisocyanate component comprising an additive with antiflocculant effect may, optionally after storage, be reacted with at least one binder component and, optionally, with further components to form, for example, paints or adhesives.

The binders may be, for example, polyacrylate polyols, polyester polyols, polyether polyols, polyurethane polyols; polyurea polyols; polyester-polyacrylate polyols; polyester-polyurethane polyols; polyurethane-polyacrylate polyols, polyurethane-modified alkyd resins; fatty acid-modified polyester-polyurethane polyols, copolymers with allyl ethers, graft polymers of the stated groups of compound having, for example, different glass transition temperatures, and also mixtures of the stated binders. Preference is given to polyacrylate polyols, polyester polyols, and polyurethane polyols.

Preferred OH numbers, measured in accordance with DIN 53240-2 (potentiometrically), are 40-350 mg KOH/g resin solids for polyesters, preferably 80-180 mg KOH/g resin solids, and 15-250 mg KOH/g resin solids for polyacrylate-ols, preferably 80-160 mg KOH/g.

Additionally the binders may have an acid number in accordance with DIN EN ISO 3682 (potentiometrically) of up to 200 mg KOH/g, preferably up to 150 and more preferably up to 100 mg KOH/g.

Particularly preferred binders are polyacrylate polyols and polyesterols.

Polyacrylate polyols preferably have a molecular weight $M_n$ of at least 500, more preferably at least 1200 g/mol. The molecular weight $M_n$ may in principle have no upper limit, and may preferably be up to 50 000, more preferably up to 20 000 g/mol, and very preferably up to 10 000 g/mol, and more particularly up to 5000 g/mol.

The hydroxyl-functional monomers (see below) are also used in the copolymerization in amounts such as to result in the aforementioned hydroxyl numbers for the polymers, which generally correspond to a hydroxyl group content in the polymers of 0.5% to 8%, preferably 1% to 5% by weight.

These are hydroxyl-containing copolymers of at least one hydroxyl-containing (meth)acrylate with at least one further polymerizable comonomer selected from the group consisting of (meth)acrylic acid alkyl esters, vinylaromatics, α,β-unsaturated carboxylic acids, and other monomers.

(Meth)acrylic acid alkyl esters include, for example, $C_1$-$C_{20}$ alkyl (meth)acrylates; vinylaromatics are those having up to 20 C atoms; α,β-unsaturated carboxylic acids also include their anhydrides; and other monomers are, for example, vinyl esters of carboxylic acids comprising up to 20 C atoms, ethylenically unsaturated nitriles, vinyl ethers of alcohols comprising 1 to 10 C atoms, and, less preferably, aliphatic hydrocarbons having 2 to 8 C atoms and 1 or 2 double bonds.

Preferred (meth)acrylic acid alkyl esters are those with a $C_1$-$C_{10}$ alkyl radical, such as methyl methacrylate, methyl acrylate, n-butyl acrylate, ethyl acrylate, and 2-ethylhexyl acrylate.

In particular, mixtures of the (meth)acrylic acid alkyl esters are suitable as well.

Vinyl esters of carboxylic acids having 1 to 20 C atoms are, for example, vinyl laurate, vinyl stearate, vinyl propionate and vinyl acetate.

Examples of possible α,β-unsaturated carboxylic acids and their anhydrides include: acrylic acid, methacrylic acid, fumaric acid, crotonic acid, itaconic acid, maleic acid or maleic anhydride, preferably acrylic acid.

Hydroxy-functional monomers include monoesters of α,β-unsaturated carboxylic acids, such as acrylic acid, methacrylic acid (identified for short in this specification as "(meth)acrylic acid"), with diols or polyols which have preferably 2 to 20 C atoms and at least two hydroxyl groups, such as ethylene glycol, diethylene glycol, triethylene glycol, 1,2-propylene glycol, 1,3-propylene glycol, 1,1-dimethyl-1,2-ethanediol, dipropylene glycol, triethylene glycol, tetraethylene glycol, pentaethylene glycol, tripropylene glycol, 1,4-butanediol, 1,5-pentanediol, neopentyl glycol, neopentyl glycol hydroxypivalate, 2-ethyl-1,3-propanediol, 2-methyl-1,3-propanediol, 2-butyl-2-ethyl-1,3-propanediol, 1,6-hexanediol, 2-methyl-1,5-pentanediol, 2-ethyl-1,4-butanediol, 2-ethyl-1,3-hexanediol, 2,4-diethyloctane-1,3-diol, 2,2-bis(4-hydroxycyclohexyl)propane, 1,1-, 1,2-, 1,3- and 1,4-bis(hydroxymethyl)cyclohexane, 1,2-, 1,3- or 1,4-cyclohexanediol, glycerol, trimethylolethane, trimethylolpropane, trimethylolbutane, pentaerythritol, ditrimethylolpropane, dipentaerythritol, sorbitol, mannitol, diglycerol, threitol, erythritol, adonitol (ribitol), arabitol (lyxitol), xylitol, dulcitol (galactitol), maltitol, isomalt, polyTHF with a molecular weight between 162 and 4500, preferably 250 to 2000, poly-1,3-propanediol or polypropylene glycol with a molecular weight between 134 and 2000, or polyethylene glycol with a molecular weight between 238 and 2000.

Preference is given to 2-hydroxyethyl acrylate, 2-hydroxyethyl methacrylate, 2- or 3-hydroxypropyl acrylate, 1,4-butanediol monoacrylate or 3-(acryloyloxy)-2-hydroxypropyl acrylate, and particular preference to 2-hydroxyethyl acrylate and/or 2-hydroxyethyl methacrylate.

Vinylaromatic compounds contemplated include, for example, vinyltoluene, α-butylstyrene, α-methylstyrene, 4-n-butylstyrene, 4-n-decylstyrene, and, preferably, styrene.

Examples of nitriles are acrylonitrile and methacrylonitrile.

Suitable vinyl ethers are, for example, vinyl methyl ether, vinyl isobutyl ether, vinyl hexyl ether, and vinyl octyl ether.

Nonaromatic hydrocarbons having 2 to 8 C atoms and one or two olefinic double bonds include butadiene, isoprene, also ethylene, propylene, and isobutylene.

Additionally it is possible to use N-vinylformamide, N-vinylpyrrolidone, and N-vinylcaprolactam, and, additionally, ethylenically unsaturated acids, more particularly carboxylic acids, acid anhydrides or acid amides, and also vinylimidazole. Comonomers containing epoxide groups, such as glycidyl acrylate or glycidyl methacrylate, or monomers such as N-methoxymethylacrylamide or -methacrylamide, can also be used as well in small amounts.

Preference is given to esters of acrylic acid and/or of methacrylic acid with 1 to 18, preferably 1 to 8, carbon atoms in the alcohol residue, such as, for example, methyl acrylate, ethyl acrylate, isopropyl acrylate, n-propyl acrylate, n-butyl acrylate, 2-ethylhexyl acrylate, n-stearyl acrylate, the methacrylates corresponding to these acrylates, styrene, alkyl-substituted styrenes, acrylonitrile, methacrylonitrile, vinyl acetate or vinyl stearate, and any desired mixtures of such monomers.

The hydroxyl-bearing monomers are used in the copolymerization of the hydroxyl-bearing (meth)acrylates in a mixture with other polymerizable monomers, preferably free-radically polymerizable monomers, preferably those composed to an extent of more than 50% by weight of $C_1$-$C_{20}$, preferably $C_1$ to $C_4$ alkyl (meth)acrylate, (meth)acrylic acid, vinylaromatics having up to 20 C atoms, vinyl esters of carboxylic acids comprising up to 20 C atoms, vinyl halides, nonaromatic hydrocarbons having 4 to 8 C atoms and 1 or 2 double bonds, unsaturated nitriles, and mixtures thereof. Particular preference is given to the polymers composed, further to the hydroxyl-bearing monomers, to an extent of more than 60% by weight of $C_1$-$C_{10}$ alkyl (meth)acrylates, styrene and its derivatives, or mixtures thereof.

The polymers can be prepared by polymerization in accordance with customary processes. Preferably the polymers are prepared in an emulsion polymerization or in organic solution. Continuous or discontinuous polymerization processes are possible. The discontinuous processes include the batch process and the feed process, the latter being preferred. In the feed process, the solvent, alone or with part of the monomer mixture, is introduced as an initial charge and heated to the polymerization temperature, the polymerization, in the case of the inclusion of monomer in the initial charge, is initiated free-radically, and the remainder of the monomer mixture is metered in together with an initiator mixture in the course of 1 to 10 hours, preferably 3 to 6 hours. A subsequent option is to carry out reactivation, in order to take the polymerization to a conversion of at least 99%.

Solvents contemplated include, for example, aromatics, such as solvent naphtha, benzene, toluene, xylene, chlorobenzene, esters such as ethyl acetate, butyl acetate, methylglycol acetate, ethylglycol acetate, methoxypropyl acetate, ethers such as butylglycol, tetrahydrofuran, dioxane, ethylglycol ether, ketones such as acetone, methyl ethyl ketone, halogenated solvents such as methylene chloride or trichloromonofluoroethane.

Further binders are, for example, polyester polyols, as are obtainable by condensing polycarboxylic acids, especially dicarboxylic acids, with polyols, especially diols. In order to ensure a polyester polyol functionality that is appropriate for the polymerization, use is also made in part of triols, tetrols, etc, and also triacids etc.

Polyester polyols are known for example from Ullmanns Enzyklopädie der technischen Chemie, 4th edition, volume 19, pp. 62 to 65. It is preferred to use polyester polyols which are obtained by reacting dihydric alcohols with dibasic carboxylic acids. In lieu of the free polycarboxylic acids it is also possible to use the corresponding polycarboxylic anhydrides or corresponding polycarboxylic esters of lower alcohols or mixtures thereof to prepare the polyester polyols. The polycarboxylic acids may be aliphatic, cycloaliphatic, aromatic or heterocyclic and may optionally be substituted, by halogen atoms for example, and/or unsaturated. Examples thereof that may be mentioned include the following:

Oxalic acid, maleic acid, fumaric acid, succinic acid, glutaric acid, adipic acid, sebacic acid, dodecanedioic acid, o-phthalic acid, isophthalic acid, terephthalic acid, trimellitic acid, azelaic acid, 1,4-cyclohexanedicarboxylic acid or tetrahydrophthalic acid, suberic acid, azelaic acid, phthalic anhydride, tetrahydrophthalic anhydride, hexahydrophthalic anhydride, tetrachlorophthalic anhydride, endomethylenetetrahydrophthalic anhydride, glutaric anhydride, maleic anhydride, dimeric fatty acids, their isomers and hydrogenation products, and also esterifiable derivatives, such as anhydrides or dialkyl esters, $C_1$-$C_4$ alkyl esters for example, preferably methyl, ethyl or n-butyl esters, of the stated acids are employed. Preference is given to dicarboxylic acids of the general formula HOOC—$(CH_2)$COOH, where y is a number from 1 to 20, preferably an even number from 2 to 20, and more preferably succinic acid, adipic acid, sebacic acid, and dodecanedicarboxylic acid.

Suitable polyhydric alcohols for preparing the polyesterols include 1,2-propanediol, ethylene glycol, 2,2-dimethyl-1,2-ethanediol, 1,3-propanediol, 1,2-butanediol, 1,3-butanediol, 1,4-butanediol, 3-methylpentane-1,5-diol, 2-ethylhexane-1,3-diol, 2,4-diethyloctane-1,3-diol, 1,6-hexanediol, Poly-THF having a molar mass of between 162 and 4500, preferably 250 to 2000, poly-1,3-propanediol having a molar mass between 134 and 1178, poly-1,2-propanediol having a molar mass between 134 and 898, polyethylene glycol having a molar mass between 106 and 458, neopentyl glycol, neopentyl glycol hydroxypivalate, 2-ethyl-1,3-propanediol, 2-methyl-1,3-propanediol, 2,2-bis (4-hydroxycyclohexyl)propane, 1,1-, 1,2-, 1,3- and 1,4-cyclohexanedimethanol, 1,2-, 1,3- or 1,4-cyclohexanediol, trimethylolbutane, trimethylolpropane, trimethylolethane, neopentyl glycol, pentaerythritol, glycerol, ditrimethylolpropane, dipentaerythritol, sorbitol, mannitol, diglycerol, threitol, erythritol, adonitol (ribitol), arabitol (lyxitol), xylitol, dulcitol (galactitol), maltitol or isomalt, which optionally may have been alkoxylated as described above.

Preferred alcohols are those of the general formula HO—$(CH_2)_x$—OH, where x is a number from 1 to 20, preferably an even number from 2 to 20. Preferred are ethylene glycol, butane-1,4-diol, hexane-1,6-diol, octane-1,8-diol and dodecane-1,12-diol. Additionally preferred is neopentyl glycol.

Also suitable, furthermore, are polycarbonate diols of the kind obtainable, for example, by reacting phosgene with an excess of the low molecular mass alcohols specified as synthesis components for the polyester polyols.

Also suitable are lactone-based polyester diols, which are homopolymers or copolymers of lactones, preferably hydroxy-terminated adducts of lactones with suitable difunctional starter molecules. Suitable lactones are preferably those which derive from compounds of the general formula HO—$(CH_2)_z$—COOH, where z is a number from 1 to 20 and where one H atom of a methylene unit may also have been substituted by a $C_1$ to $C_4$ alkyl radical. Examples are ε-caprolactone, β-propiolactone, gamma-butyrolactone and/or methyl-ε-caprolactone, 4-hydroxybenzoic acid, 6-hydroxy-2-naphthoic acid or pivalolactone, and mixtures thereof. Examples of suitable starter components include the low molecular mass dihydric alcohols specified above as a synthesis component for the polyester polyols. The corresponding polymers of ε-caprolactone are particularly preferred. Lower polyester diols or polyether diols as well can be used as starters for preparing the lactone polymers. In lieu of the polymers of lactones it is also possible to use the corresponding, chemically equivalent polycondensates of the hydroxycarboxylic acids corresponding to the lactones.

In polyurethane coatings, molar masses $M_n$ of the polyesters of 800-4000 g/mol are customary, although the polyesters used here are not restricted to this range.

Additionally suitable as binders are polyetherols, which are prepared by addition reaction of ethylene oxide, propylene oxide and/or butylene oxide, preferably ethylene oxide and/or propylene oxide, and more preferably ethylene oxide, with H-active components. Polycondensates of butanediol are also suitable. In polyurethane coatings, polyether molar masses of 500-2000 g/mol are customary, although the polyethers used here are not restricted to this range.

The polymers may be replaced at least in part by what are called reactive diluents. These may be blocked secondary or primary amines (aldimines and ketimines) or compounds having sterically hindered and/or electron-deficient secondary amino groups, examples being aspartic esters as per EP 403921 or WO 2007/39133.

After mixing of the polyisocyanate component with a binder component and optionally further components, the coating mixture is cured at from ambient temperature to 150° C.

"Curing" in the context of the present invention means the generation of a tack-free coating on a substrate by the heating of the coating composition applied to the substrate at the temperature indicated above for at least long enough for the desired tack-free state to be established.

In one preferred form, in the context of the present specification, a coating composition means a mixture of at least two components (binder and crosslinker) which is intended for the coating of at least one substrate for the purpose of forming a film and, after curing, a tack-free coating.

The substrates are coated by typical methods known to the skilled person, with at least one coating composition being applied in the desired thickness to the substrate to be coated, and any volatile constituents of the coating composition being removed, optionally with heating. This operation may if desired be repeated one or more times. Application to the substrate may take place in a known way, as for example by spraying, troweling, knifecoating, brushing, rolling, rollercoating, flowcoating, laminating, injection backmolding or coextruding.

The thickness of a film of this kind for curing may be from 0.1 μm up to several mm, preferably from 1 to 2000 μm, more preferably 5 to 200 μm, very preferably from 5 to 60 μm (based on the coating material in the state in which the solvent has been removed from the coating material).

Additionally provided by the present invention are substrates coated with a multicoat paint system of the invention.

Polyurethane coating materials of this kind are especially suitable for applications requiring particularly high application reliability, exterior weathering resistance, optical qualities, solvent resistance, chemical resistance, and water resistance.

The two-component coating compositions and coating formulations obtained are suitable for coating substrates such as wood, wood veneer, paper, cardboard, paperboard, textile, film, leather, nonwoven, plastics surfaces, glass, ceramic, mineral building materials, such as molded cement blocks and fiber-cement slabs, or metals, which in each case may optionally have been precoated or pretreated.

Coating compositions of this kind are suitable as or in interior or exterior coatings, i.e., in those applications where there is exposure to daylight, preferably of parts of buildings, coatings on (large) vehicles and aircraft, and industrial applications, utility vehicles in agriculture and construction, decorative coatings, bridges, buildings, power masts, tanks, containers, pipelines, power stations, chemical plants, ships, cranes, posts, sheet piling, valves, pipes, fittings, flanges, couplings, halls, roofs, and structural steel, furniture, windows, doors, woodblock flooring, can coating and coil coating, for floor coverings, such as in parking levels or in hospitals, in automotive finishes, as OEM and refinish.

In one preferred form, coating compositions of this kind are used at temperatures between ambient temperature to 80° C., preferably to 60° C., more preferably to 40° C. The articles in question are preferably those which cannot be cured at high temperatures, such as large machines, aircraft, large-capacity vehicles, and refinish applications. Ambient temperature is taken customarily to be the temperature at which the coated substrate is used in the manner intended.

In another preferred application, the coating mixture is cured at 110-150° C., preferably at 120-140° C. (e.g., for OEM applications).

In particular the coating compositions of the invention are used as clearcoat, basecoat, and topcoat material(s), primers, and surfacers.

Long storage of the polyisocyanate component is customary especially with refinish applications and in some cases with industrial applications as well. The polyisocyanate admixed with additives with antiflocculant effect, or the polyisocyanate component, can of course also be used for any other application.

EXAMPLES

Ingredients:
Polyisocyanates (A): isocyanurate based on hexamethylene diisocyanate
Polyisocyanate (A1), polyisocyanurate based on hexamethylene diisocyanate: Hexamethylene diisocyanate HDI was reacted in the presence of 80 ppm by weight of benzyltrimethylammonium hydroxyisobutyrate as catalyst, based on hexamethylene diisocyanate, at 60% strength in ethylene glycol, in a multi-stage reactor cascade at 115, 120 and 130° C. Hexamethylene diisocyanate was distilled off in a multistage process with HDI recirculation. NCO content of the product: 22.2%, viscosity: 2675 mPa*s.
Polyisocyanate (A2): polyisocyanurate based on hexamethylene diisocyanate Basonat HI 100 BASF SE
Silyl Derivatives:

| | | |
|---|---|---|
| Tristrimethylsilyl phosphate | Sigma-Aldrich | inventive |
| N,O-bis(trimethylsilyl) acetamide | Sigma-Aldrich | not inventive |
| 1,3-bis(trimethylsilyl)urea | Sigma-Aldrich | not inventive |
| Hexamethyldisilazane | Sigma-Aldrich | not inventive |

Solvents (C):
  Xylene
  Butyl acetate
Sterically Hindered Phenols:
Irganox® 1010: pentaerythritol tetrakis(3-(3,5-di-tert-butyl-4-hydroxyphenyl)propionate), BASF SE
Irganox® 1076: octadecyl 3-(3,5-di-tert-butyl-4-hydroxyphenyl)propionate), BASF SE
Irganox® 1135: isooctyl 3-(3,5-di-tert-butyl-4-hydroxyphenyl)propionate), BASF SE
Secondary Antioxidants:

| | |
|---|---|
| Irgafos OPH | BASF SE |
| Triphenyl phosphite | Alfa Aesar |
| Tributyl phosphite | Sigma-Aldrich |

Storage Test:
For determining the flocculation stability, mixtures consisting of 30% polyisocyanate and 70% xylene/butyl acetate=2:1, containing 400 ppm of water to solvent mixture, were prepared. Additives were incorporated via the solvents. 50 g of the mixture was rendered inert by the passage of nitrogen over it in 50 mL screw lid vessels without writing on the side, which were then firmly closed and stored at 23° C.±5° C./(50%±10% atmospheric humidity) in a climatic chamber. The flocculation was assessed by inspection daily on weekdays in the first two weeks, after three weeks, from four weeks onward, at two-week intervals.

To assess the flocculation stability, a report is made of the first day on which one of the two following flocculation stages is achieved:
1 Slight flocculation: weakly apparent. For better recognition of turbidity, apparently clear solutions are briefly slightly horizontally rotated in a circle. In some cases slight flocculation is then evident better as a tail.

2 Severe flocculation, readily apparent, sedimentation, discontinuation of the study.

Although the flocculation is determined by experienced personnel, a certain standard deviation is nevertheless present, as a consequence of slight differences in conditions (e.g., exact amount of water in the solvent, etc.) and in the visual determination of slight and severe turbidity. In different series there may be slightly different results for specimens with "the same" composition, but in terms of the number of days these specimens are nevertheless all comparable, and are much lower in the proportion of good examples to poor references.

The day values for the two flocculation stages are additionally added up for a better comparison. The greater the number of day values or the total thereof, the better the flocculation stability. At 210 days of measurement, measurement is terminated automatically.

Series 1: Polyisocyanate (A1): Flocculation Times in Days after a Maximum of 210 Days of Measurement

| Fl./d | Additive (ppm) | 1 | 2 | Total |
|---|---|---|---|---|
| C1 | 200 Irganox 1135 | 28 | 28 | 56 |
| I1 | 200 Irganox 1135 + 100 tristrimethylsilyl phosphate | 84 | 196 | 280 |
| C2 | 200 triphenyl phosphite | 2 | 98 | 100 |
| I2 | 200 triphenyl phosphite + 100 tristrimethylsilyl phosphate | 84 | 210 | 294 |
| C3 | 200 Irganox 1076 + 200 triphenyl phosphite | 12 | 21 | 33 |
| I3 | 200 Irganox 1076 + 200 triphenyl phosphite + 100 tristrimethylsilyl phosphate | 12 | 210 | 222 |
| C4 | 200 Irganox 1135 + 200 triphenyl phosphite | 6 | 28 | 34 |
| I4 | 200 Irganox 1135 + 200 triphenyl phosphite + 50 tristrimethylsilyl phosphate | 126 | 210 | 336 |
| I5 | 200 Irganox 1135 + 200 triphenyl phosphite + 100 tristrimethylsilyl phosphate | 84 | 210 | 294 |
| C5 | 200 Irganox 1076 + 200 Irgafos OPH | 28 | 28 | 56 |
| I6 | 200 Irganox 1076 + 200 Irgafos OPH + 100 tristrimethylsilyl phosphate | 56 | 182 | 238 |
| C6 | 200 Irganox 1010 + 200 Irgafos OPH | 42 | 42 | 84 |
| I7 | 200 Irganox 1010 + 200 ppm Irgafos OPH + 100 tristrimethylsilyl phosphate | 84 | 210 | 294 |

Result: Tristrimethylsilyl phosphate improves the flocculation in combination with at least one respective antioxidant.

Series 2: Polyisocyanate (A2): Flocculation Times in Days after a Maximum of 210 Days of Measurement

| Fl./d | Additive (ppm) | 1 | 2 | Total |
|---|---|---|---|---|
| C7 | none | 11 | 21 | 32 |
| I8 | 50 tristrimethylsilyl phosphate | 56 | 210 | 266 |
| I9 | 100 tristrimethylsilyl phosphate | 28 | 210 | 238 |
| C8 | 200 Irganox 1135 | 8 | 21 | 29 |
| I10 | 200 Irganox 1135 + 100 tristrimethylsilyl phosphate | 28 | 210 | 238 |
| C9 | 200 triphenyl phosphite | 14 | 21 | 35 |
| I11 | 200 triphenyl phosphite + 100 tristrimethylsilyl phosphate | 56 | 154 | 210 |
| C10 | 200 Irgafos OPH | 21 | 21 | 42 |
| I12 | 200 Irgafos OPH + 100 tristrimethylsilyl phosphate | 56 | 210 | 266 |
| C11 | 200 Irganox 1135 + 200 tributyl phosphite | 21 | 21 | 42 |
| I13 | 200 Irganox 1135 + 200 tributyl phosphite + 100 tristrimethylsilyl phosphate | 13 | 210 | 223 |
| C12 | 200 Irganox 1010 + 200 triphenyl phosphite | 28 | 42 | 70 |
| I14 | 200 Irganox 1010 + 200 triphenyl phosphite + 100 tristrimethylsilyl phosphate | 28 | 196 | 224 |
| C13 | 200 Irganox 1076 + 200 triphenyl phosphite | 12 | 42 | 54 |
| I15 | 200 Irganox 1076 + 200 triphenyl phosphite + 100 tristrimethylsilyl phosphate | 9 | 126 | 135 |
| C14 | 200 Irganox 1135 + 200 triphenyl phosphite | 8 | 21 | 29 |
| I16 | 200 Irganox 1135 + 200 triphenyl phosphite + 50 tristrimethylsilyl phosphate | 8 | 210 | 218 |
| C15 | 200 Irganox 1135 + 200 triphenyl phosphite + 300 tristrimethylsilyl phosphate | 7 | 8 | 15 |
| C16 | 200 Irganox 1135 + 200 triphenyl phosphite + 1000 tristrimethylsilyl phosphate | 5 | 5 | 10 |

Result: (50 and) 100 ppm of tristrimethylsilyl phosphate improve the flocculation without antioxidant, with one respective antioxidant, and with two respective antioxidants.

300 and 1000 ppm of tristrimethylsilyl phosphate have adverse effects in combination with 200 Irganox® 1135+200 triphenyl phosphite.

Series 3: Polyisocyanate (A1): Flocculation Times in Days after a Maximum of 126 Days of Measurement (Termination Owing to Flocculation)

| Fl./d | Additives (ppm) | 1 | 2 | Total |
|---|---|---|---|---|
| C17 | 200 Irganox 1135 + 200 Irgafos OPH | 21 | 21 | 42 |
| C18 | 200 Irganox 1135 + 200 Irgafos OPH + 100 N,O-bis(trimethylsilyl)acetamide | 5 | 13 | 18 |
| C19 | 200 Irganox 1135 + 200 Irgafos OPH + 100 1,3-bis(trimethylsilyl)urea | 9 | 13 | 22 |
| C20 | 200 Irganox 1135 + 200 Irgafos OPH + 100 hexamethyldisilazane | 9 | 13 | 22 |
| I17 | 200 Irganox 1135 + 200 Irgafos OPH + 100 tristrimethylsilyl phosphate | 12 | 126 | 138 |

Result: 100 ppm of tristrimethylsilyl phosphate improve the flocculation; N,O-bis(trimethylsilyl)acetamide, hexamethyldisilazane, and 1,3-bis(trimethylsilyl)urea do not.

Series 4: Polyisocyanate (A1): Flocculation Times in Days after a Maximum of 210 Days of Measurement

| Fl./d | Additives (ppm) | 1 | 2 | Total |
|---|---|---|---|---|
| C21 | 200 Irganox 1135 + 200 Irgafos OPH | 7 | 14 | 21 |
| C22 | 200 Irganox 1135 + 200 Irgafos OPH + 1 tristrimethylsilyl phosphate | 7 | 11 | 18 |
| I18 | 200 Irganox 1135 + 200 Irgafos OPH + 5 tristrimethylsilyl phosphate | 14 | 56 | 70 |
| I19 | 200 Irganox 1135 + 200 Irgafos OPH + 10 tristrimethylsilyl phosphate | 126 | 210 | 336 |
| I20 | 200 Irganox 1135 + 200 Irgafos OPH + 20 tristrimethylsilyl phosphate | 14 | 210 | 224 |
| I21 | 200 Irganox 1135 + 200 Irgafos OPH + 50 tristrimethylsilyl phosphate | 14 | 182 | 196 |
| I22 | 200 Irganox 1135 + 200 Irgafos OPH + 100 tristrimethylsilyl phosphate | 2 | 182 | 184 |
| C23 | 200 Irganox 1135 + 200 Irgafos OPH + 300 tristrimethylsilyl phosphate | 2 | 9 | 11 |
| C24 | 200 Irganox 1135 + 200 Irgafos OPH + 1000 tristrimethylsilyl phosphate | 2 | 7 | 9 |

Result: 5 ppm of tristrimethylsilyl phosphate improve flocculation slightly, 10, 20, 50 and 100 ppm of tristrimethylsilyl phosphate do so very significantly. 300 and 1000 ppm have nonpositive or negative effects.

Series 5: Polyisocyanate (A2): Flocculation Times in Days after a Maximum of 210 Days of Measurement

| Fl./d | Additives (ppm) | 1 | 2 | Total |
|---|---|---|---|---|
| C25 | 200 Irganox 1135 + 200 Irgafos OPH | 7 | 21 | 28 |
| I23 | 200 Irganox 1135 + 200 Irgafos OPH + 1 tristrimethylsilyl phosphate | 7 | 56 | 63 |
| I24 | 200 Irganox 1135 + 200 Irgafos OPH + 5 tristrimethylsilyl phosphate | 56 | 210 | 266 |
| I25 | 200 Irganox 1135 + 200 Irgafos OPH + 10 tristrimethylsilyl phosphate | 21 | 210 | 231 |
| I26 | 200 Irganox 1135 + 200 Irgafos OPH + 20 tristrimethylsilyl phosphate | 21 | 210 | 231 |
| I27 | 200 Irganox 1135 + 200 Irgafos OPH + 50 tristrimethylsilyl phosphate | 7 | 210 | 217 |
| I28 | 200 Irganox 1135 + 200 Irgafos OPH + 100 tristrimethylsilyl phosphate | 7 | 210 | 217 |
| C26 | 200 Irganox 1135 + 200 Irgafos OPH + 300 tristrimethylsilyl phosphate | 7 | 8 | 15 |
| C27 | 200 Irganox 1135 + 200 Irgafos OPH + 1000 tristrimethylsilyl phosphate | 7 | 7 | 14 |

Result: 1 ppm of tristrimethylsilyl phosphate slightly improves flocculation. From 5 ppm upward of tristrimethylsilyl phosphate, the improvement is very significant. 300 and 1000 ppm of tristrimethylsilyl phosphate have negative effects again.

The invention claimed is:

1. A method for reducing flocculation and/or precipitation in a polyisocyanate mixture which comprises at least one solvent (C) and at least one polyisocyanate (A) comprising a polyisocyanurate based on hexamethylene diisocyanate, the method comprising adding, to the polyisocyanate mixture, tristrimethylsilyl phosphate, in an amount of 10 to 100 ppm by weight based on the at least one polyisocyanate (A), to obtain a polyisocyanate mixture comprising the tristrimethylsilyl phosphate.

2. The method of claim 1, wherein the tristrimethylsilyl phosphate is used substoichiometrically in relation to an amount of water present in the polyisocyanate mixture.

3. The method of claim 1, wherein the at least one polyisocyanate (A) has an NCO content of at least 15% by weight.

4. The method of claim 1, wherein the polyisocyanate mixture comprising the tristrimethylsilyl phosphate further comprises at least one phenol or bridged bisphenol which has exactly one phenolic hydroxyl group on each aromatic ring and has alkyl groups in the positions ortho to each phenolic hydroxyl group.

5. The method of claim 1, wherein the polyisocyanate mixture comprising the tristrimethylsilyl phosphate further comprises at least one Lewis acid.

6. The method of claim 1, wherein the polyisocyanate mixture comprises at least one antioxidant selected from the group consisting of sterically hindered phenols, phosphonites, and phosphonates.

7. A method for stabilizing a polyisocyanate mixture which comprises at least one solvent (C) and at least one polyisocyanate (A) comprising a polyisocyanurate based on hexamethylene diisocyanate against flocculation during storage, the method comprising admixing the polyisocyanate mixture with tristrimethylsilyl phosphate, in an amount of 10 to 100 ppm by weight based on the at least one polyisocyanate (A).

8. The method of claim 7, wherein the polyisocyanate mixture comprises at least one Lewis acid.

9. A method for coating a substrate with a polyisocyanate mixture which comprises at least one polyisocyanate (A) comprising a polyisocyanurate based on hexamethylene diisocyanate and is stabilized against flocculation during storage in a solvent, the method comprising:
   admixing the polyisocyanate mixture with tristrimethylsilyl phosphate, in an amount of 10 to 100 ppm by weight based on the at least one polyisocyanate (A), to obtain a mixture;
   admixing the mixture with at least one solvent (C) and optionally other additives, to obtain a composition;
   storing the composition, to obtain a stored composition;
   subsequently admixing the stored composition with at least one binder-comprising component, to obtain an admixed composition; and
   subsequently applying the admixed composition to a substrate.

10. The method of claim 9, wherein the at least one binder-comprising component comprises a polymer selected from the group consisting of a polyacrylate polyol, a polyester polyol, a polyurethane polyol, a polycarbonate polyol and a polyether polyol.

* * * * *